United States Patent [19]
Reid et al.

[11] Patent Number: 5,575,811
[45] Date of Patent: *Nov. 19, 1996

[54] BENIGN PROSTATIC HYPERPLASIA TREATMENT CATHETER WITH URETHRAL COOLING

[75] Inventors: John M. Reid, Minnetrista; James V. Kauphusman, Champlin, both of Minn.; Christopher H. Porter, Woodinville, Wash.; Bruce H. Neilson, Brooklyn Park, Minn.

[73] Assignee: Urologix, Inc., Minneapolis, Minn.

[*] Notice: The term of this patent shall not extend beyond the expiration date of Pat. No. 5,464,437.

[21] Appl. No.: 447,374

[22] Filed: May 23, 1995

Related U.S. Application Data

[63] Continuation of Ser. No. 88,901, Jul. 8, 1993, Pat. No. 5,464,437.

[51] Int. Cl.$^6$ .................................................. A61N 5/02
[52] U.S. Cl. .................... 607/101; 607/102; 607/105; 607/113; 607/156
[58] Field of Search ............................. 607/100–102, 607/105, 113, 156

[56] References Cited

U.S. PATENT DOCUMENTS

| | | | |
|---|---|---|---|
| 550,238 | 11/1895 | Allen, Jr. . | |
| 2,652,874 | 6/1953 | Keeling | 128/349 |
| 2,813,531 | 11/1957 | Lee | 128/350 |
| 2,936,761 | 5/1960 | Snyder | 128/349 |
| 3,812,841 | 5/1974 | Isaacson | 128/1 R |
| 3,977,408 | 8/1976 | MacKew | 128/349 B |
| 4,224,929 | 9/1980 | Furihata | 128/5 |
| 4,290,435 | 9/1981 | Waggott | 128/800 |
| 4,423,725 | 1/1984 | Baran et al. | 128/207.15 |
| 4,430,083 | 2/1984 | Ganz et al. | 604/283 |
| 4,445,892 | 5/1984 | Hussein et al. | 604/101 |
| 4,453,545 | 6/1984 | Inove | 128/207.15 |
| 4,573,966 | 3/1986 | Weikl et al. | 604/53 |
| 4,610,662 | 9/1986 | Weikl et al. | 604/53 |
| 4,655,746 | 4/1987 | Daniels et al. | 604/53 |
| 4,708,718 | 11/1987 | Daniels | 604/20 |
| 4,709,698 | 12/1987 | Johnston et al. | 128/303.12 |
| 4,753,238 | 6/1988 | Gaiser | 128/344 |
| 4,763,654 | 8/1988 | Jang | 128/344 |
| 4,771,777 | 9/1988 | Horzewski et al. | 128/344 |
| 4,777,951 | 10/1988 | Cribier et al. | 128/344 |
| 4,823,812 | 4/1989 | Eshel et al. | 128/804 |
| 4,824,436 | 4/1989 | Wolinsky | 604/53 |
| 4,832,688 | 5/1989 | Sagae et al. | 604/53 |
| 4,896,670 | 1/1990 | Crittenden | 606/194 |
| 4,911,163 | 3/1990 | Fina | 606/127 |
| 4,921,483 | 5/1990 | Wijay et al. | 604/96 |
| 4,932,958 | 6/1990 | Reddy et al. | 606/192 |
| 4,961,738 | 10/1990 | Mackin | 606/15 |
| 4,967,765 | 11/1990 | Turner et al. | 128/785 |
| 4,993,430 | 2/1991 | Shimoyama et al. | 128/784 |
| 5,002,531 | 3/1991 | Bonzel | 604/96 |
| 5,002,532 | 3/1991 | Gaiser | 604/101 |
| 5,003,991 | 4/1991 | Takayama et al. | 128/784 |
| 5,007,437 | 4/1991 | Sterzer | 428/786 |
| 5,045,056 | 9/1991 | Behl | 604/49 |
| 5,056,531 | 10/1991 | Shimoyama | 128/784 |
| 5,057,106 | 10/1991 | Kasevich et al. | 606/33 |
| 5,061,267 | 10/1991 | Zeiher | 606/40 |
| 5,106,360 | 4/1992 | Ishiwara et al. . | |
| 5,129,883 | 7/1992 | Black . | |
| 5,151,100 | 9/1992 | Abele et al. . | |
| 5,234,004 | 8/1993 | Hascoet et al. . | |
| 5,300,099 | 4/1994 | Rudie . | |
| 5,304,214 | 4/1994 | Deford et al. . | |
| 5,344,435 | 9/1994 | Turner et al. . | |
| 5,464,437 | 11/1995 | Reid et al. | 607/101 |

FOREIGN PATENT DOCUMENTS

| | | | |
|---|---|---|---|
| 9111975 | 8/1991 | WIPO | 607/113 |

*Primary Examiner*—Lee S. Cohen
*Attorney, Agent, or Firm*—Kinney & Lange, P.A.

[57] ABSTRACT

A system for treatment of benign prostatic hyperplasia within intraprostatic tissue surrounding a urethra is disclosed. The system includes an intraurethral catheter having an intraurethral catheter shaft. An antenna is located within the catheter shaft for delivering heat to the intraprostatic tissue surrounding the urethra. Coolant fluid is circulated through a chamber located between the catheter shaft and the urethral wall.

18 Claims, 7 Drawing Sheets

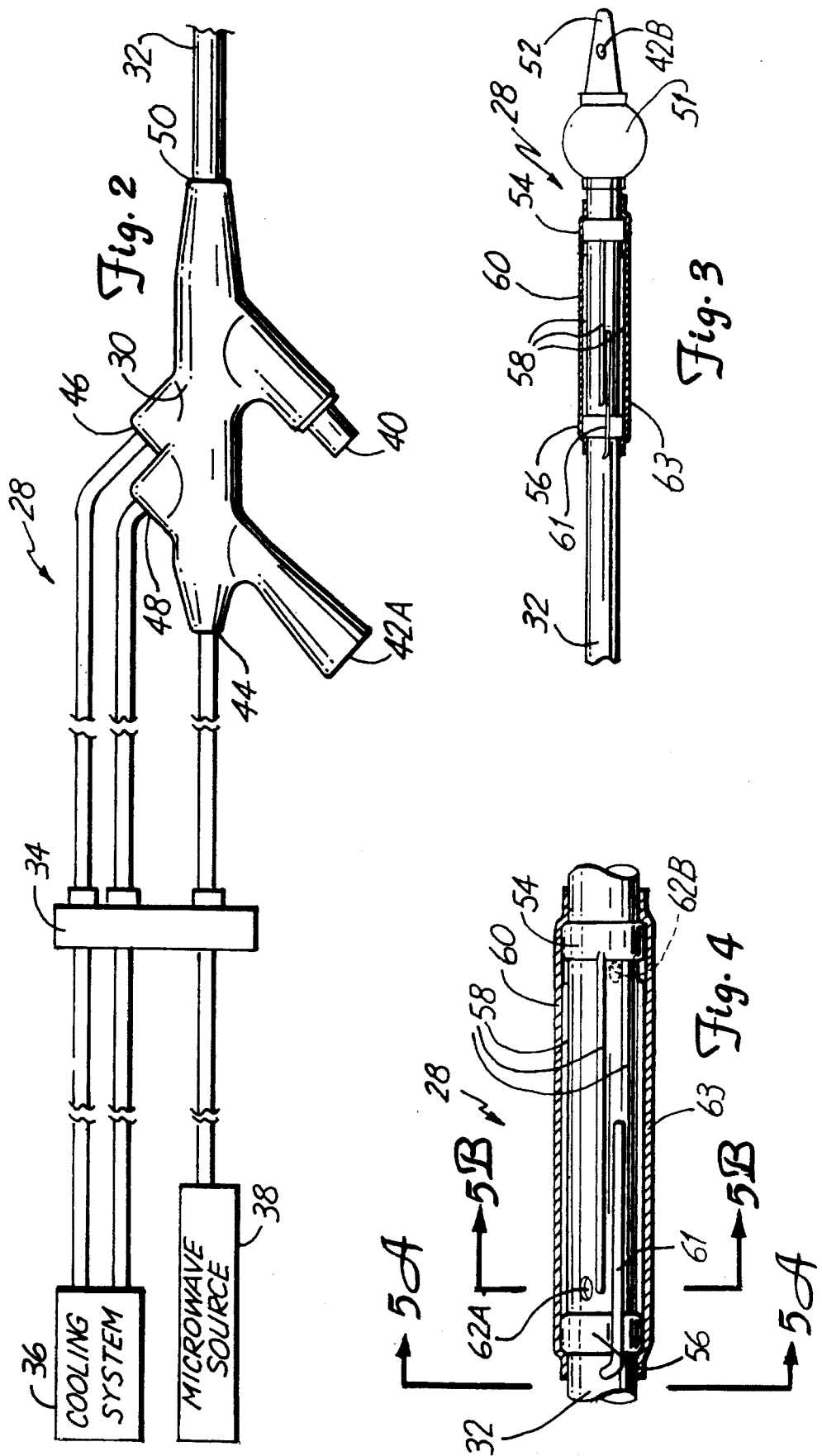

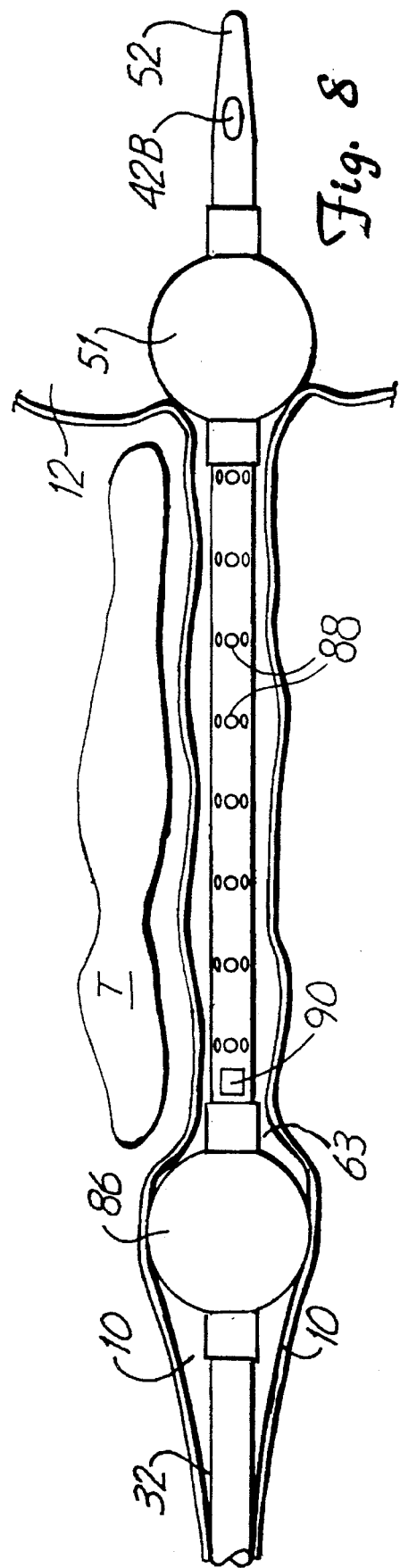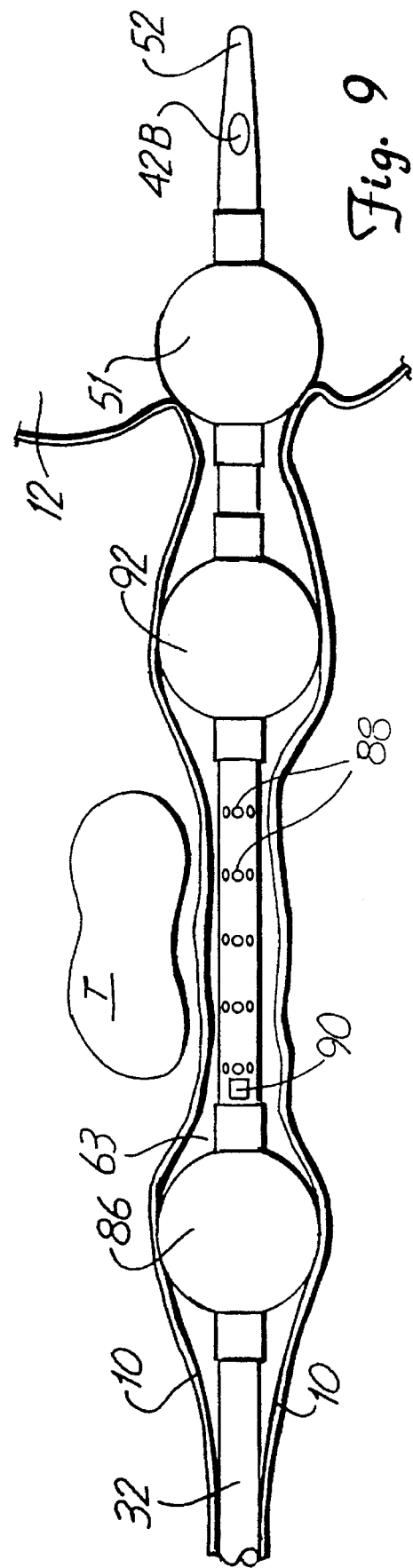

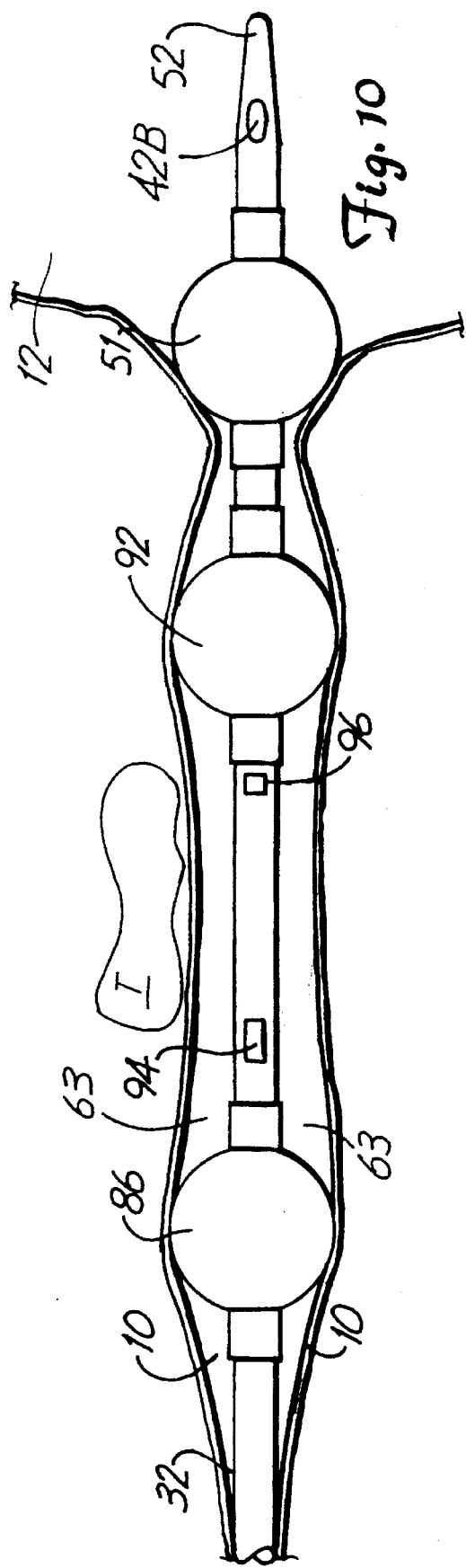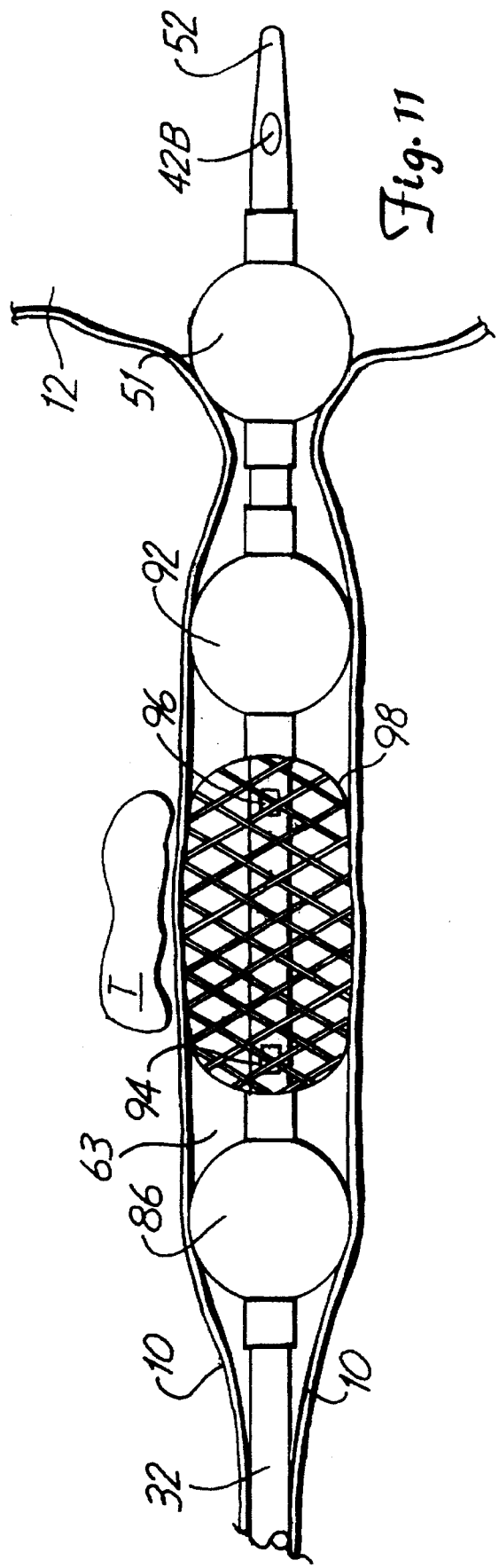

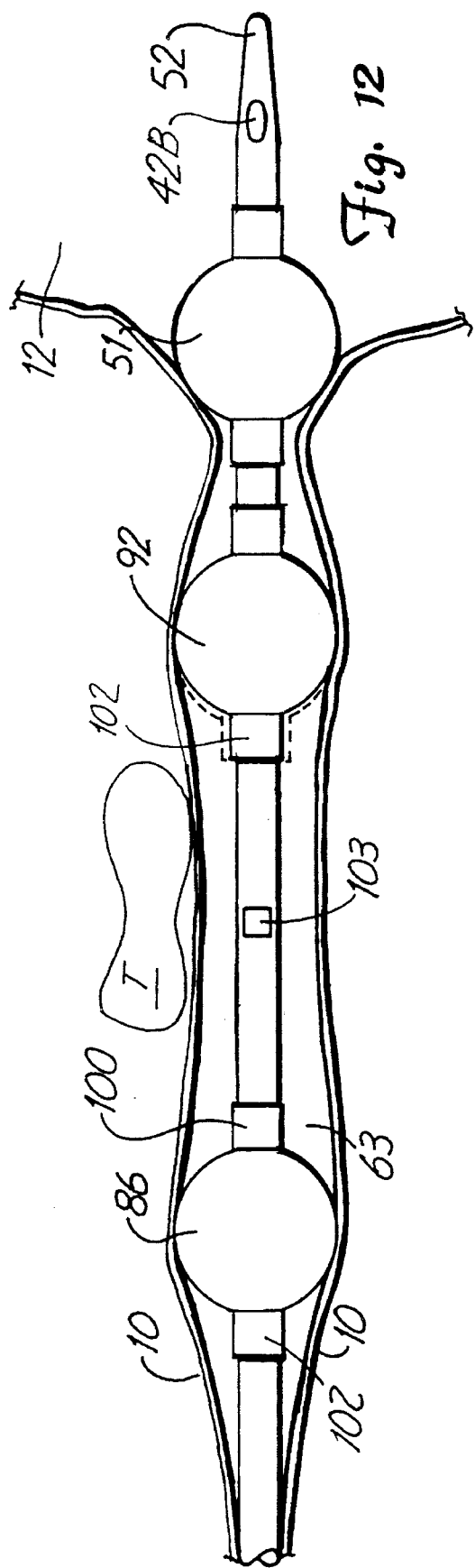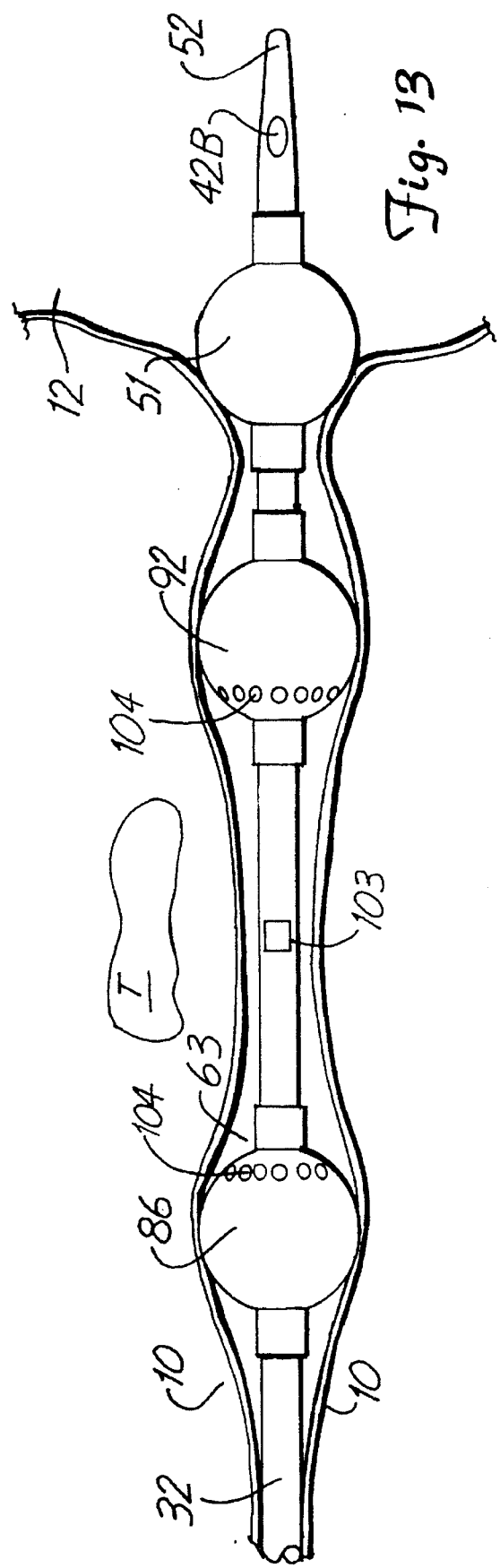

BENIGN PROSTATIC HYPERPLASIA TREATMENT CATHETER WITH URETHRAL COOLING

This is a continuation of application Ser. No. 08/088,901, filed Jul. 8, 1993, now U.S. Pat No. 5,464,437

REFERENCE TO CO-PENDING APPLICATIONS

Reference is made to the following co-pending U.S. Patent applications: Ser. No. 07/847,718, filed Mar. 6, 1992, entitled DEVICE FOR ASYMMETRICAL THERMAL THERAPY WITH HELICAL DIPOLE MICROWAVE ANTENNA, by E. Rudie et al.; Ser. No. 07/847,894, filed Mar. 6, 1992, entitled METHOD FOR TREATING INTERSTITIAL TISSUE ASSOCIATED WITH MICROWAVE THERMAL THERAPY, by B. Neilson et al; and Ser. No. 07/847,915, filed Mar. 6, 1992, entitled GAMMA MATCHED, HELICAL DIPOLE MICROWAVE ANTENNA, by E. Rudie et al.

BACKGROUND OF THE INVENTION

The present invention relates to the field of microwave thermal therapy of tissue, and in particular to a catheter for transurethral microwave thermal therapy of benign prostatic hyperplasia (BPH).

The prostate gland is a complex, chestnut shaped organ which encircles the urethra immediately below the bladder. Nearly one-third of the prostate tissue anterior to the urethra consists of fibromuscular tissue that is anatomically and functionally related to the urethra and bladder. The remaining two-thirds of the prostate is generally posterior to the urethra and consists of glandular tissue.

This relatively small organ, which is the most frequently diseased of all internal organs, is the site of a common affliction among older men: benign prostatic hyperplasia (BPH). BPH is a nonmalignant, bilateral nodular expansion of the prostate tissue in the transition zone, a periurethral region of the prostate between the fibromuscular tissue and the glandular tissue. The degree of nodular expansion within the transition zone tends to be greatest anterior and lateral to the urethra, relative to the posterior-most region of the urethra.

Left untreated, BPH causes obstruction of the urethra which can result in increased urinary frequency, urgency, incontinence; nocturia, and a slow or interrupted urinary stream. BPH may also result in more severe complications, such as urinary tract infection, acute urinary retention, hydronephrosis, and uraemia.

Traditionally, the most common treatment for BPH has been a surgical operation known as TURP (transurethral resection of the prostate). During TURP surgery, a portion of the healthy urethra is removed in order to gain access to the tumorous prostate tissue. A heated cauterizing scope is then inserted through the tip of the penis and into the urethra to remove the tumorous prostatic tissue. After the surgery, the patient is required to stay in the hospital for several days, wearing a catheter. TURP surgery, however, is often not an available method of treatment for a variety of reasons. First, due to the advanced age of many patients with BPH, other health problems such as cardiovascular disease can warrant against surgical intervention. Second, potential complications and side effects associated with transurethral surgery such as hemorrhaging, anesthetic complications, urinary infections, dysuria, incontinence, and retrograde ejaculation can adversely affect a patient's willingness to undergo such a procedure.

A fairly recent alternative method of treatment for BPH involves microwave thermal therapy, in which microwave energy is employed to elevate the temperature of tissue surrounding the prostatic urethra above about 45° C., thereby thermally damaging the tumorous tissue. Delivery of microwave energy to tumorous prostatic tissue is generally accomplished by a microwave antenna-containing applicator positioned within a body cavity adjacent the prostate gland. The microwave antenna, when energized, heats adjacent tissue due to molecular excitation and generates a cylindrically symmetrical radiation pattern which encompasses and necroses the tumorous intraprostatic tissue. The necrosed intraprostatic tissue is subsequently reabsorbed by the body, thereby relieving an individual from the systems of BPH.

One method of microwave thermal therapy described in the art includes intrarectal insertion of a microwave antenna-containing applicator. Heat generated by the antenna's electromagnetic field is monitored by a sensor which is positioned near the prostate gland by a urethral catheter. However, due to the distance between the rectum and the tumorous prostatic tissue of the transition zone, healthy intervening tissue within the cylindrically symmetrical radiation pattern is thermally damaged in the course of the intrarectal treatment.

A safer and more effective treatment of BPH is transurethral microwave thermal therapy. This method of treatment minimizes the distance between a microwave antenna-carrying applicator and the transition zone of the prostate by positioning a Foley-type catheter-bearing applicator adjacent to the prostate gland within the urethra. Due to the close proximity of the microwave antenna to the prostate, a lesser volume of healthy tissue is exposed to the cylindrically symmetrical radiation pattern generated by the microwave antenna. Therefore, the amount of healthy tissue necrosed is reduced. Transurethral applicators of the type described can be found in the previously mentioned co-pending applications.

While transurethral microwave thermal therapy reduces the distance between a microwave antenna-carrying applicator and the transition zone of the prostate gland, there is still concern that healthy tissue located between the applicator and the prostate gland may be thermally damaged. In particular, it is important that the urethral wall adjacent the applicator, which is healthy, normal tissue, not be necrosed.

SUMMARY OF THE INVENTION

The present invention is a urethral catheter which provides cooling fluid to a chamber located between the catheter shaft and the urethra wall. The catheter preferably includes a flexible catheter shaft and an antenna carried by the catheter shaft for delivering heat to the intraprostatic tissue having benign prostatic hyperplasia surrounding the urethra. Cooling fluid is circulated through the shaft to the chamber for cooling a portion of the urethra wall located adjacent the chamber. In preferred embodiments, the chamber is defined by a sleeve or by balloons attached to the catheter shaft.

BRIEF DESCRIPTION OF THE DRAWINGS

FIG. 2 is a side view of the distal end of the urethral catheter of the present invention.

FIG. 3 is a side view, partly in section, of the proximal end of the urethral catheter of the present invention.

FIG. 4 is an enlarged, partial sectional view of a portion of the urethral catheter of the present invention.

FIG. 8 is a diagram illustrating a first alternate embodiment of the present invention.

FIG. 9 is a diagram illustrating of a second alternate embodiment of the present invention.

FIG. 10 is a diagram illustrating of a third alternate embodiment of the present invention.

FIG. 11 is a diagram illustrating of a fourth alternate embodiment of the present invention.

FIG. 12 is a diagram illustrating of a fifth alternate embodiment of the present invention.

FIG. 13 is a diagram illustrating of a sixth alternate embodiment of the present invention.

DETAILED DESCRIPTION OF THE PREFERRED EMBODIMENTS

Figure 1:
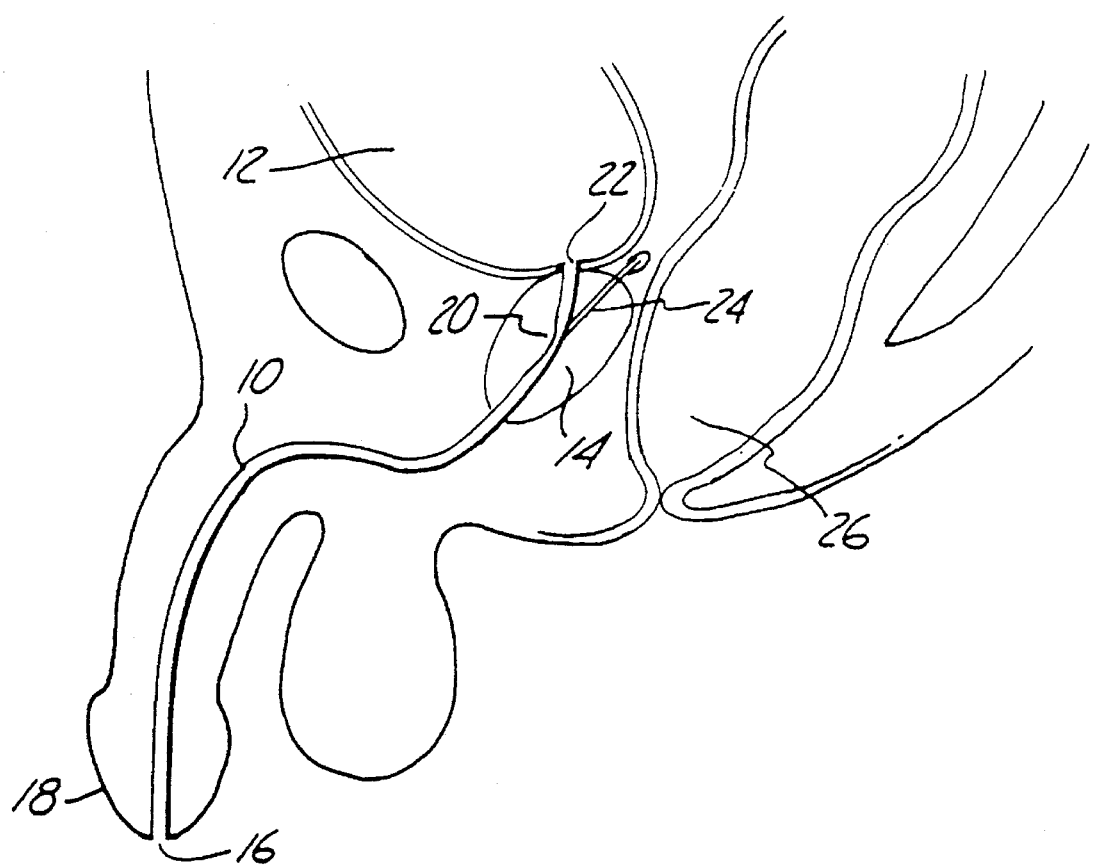
FIG. 1 is a vertical perspective view of a male pelvic region showing the urinary organs affected by benign prostate hyperplasia.

FIG. 1 is a perspective view of a male pelvic region showing the effect benign prostatic hyperplasia (BPH) has on the urinary organs. FIG. 1 includes urethra 10, bladder 12, prostate 14, orifice 16, penis end 18, constriction 20, bladder opening 22, ejaculatory duct 24, and rectum 26.

As shown in FIG. 1, urethra 10 is a duct leading from bladder 12, through prostate 14 and out orifice 16 of penis end 18. Benign tumorous tissue growth within prostate 14 around urethra 10 causes constriction 20 of urethra 10, which interrupts the flow of urine from bladder opening 22 of bladder 12 to orifice 16. The tumorous tissue of prostate 14 which encroaches urethra 10 and causes constriction 20 can be effectively removed by heating and necrosing the encroaching tumorous tissue. Ideally, only paraurethral tumorous tissue of prostate 14 anterior and lateral to urethra 10 is heated and necrosed to avoid unnecessary and undesirous damage to urethra 10 and to adjacent healthy tissues, such as ejaculatory duct 24 and rectum 26. Transurethral thermal therapy, which entails selectively heating benign prostatic hyperplasia within intraprostatic tissue surrounding urethra 10, is made possible by microwave antenna-carrying urethral catheter 28 of the present invention. Urethral catheter 28 is shown in FIGS. 2 and 3.

FIG. 2 is a side view of the distal end of urethral catheter 28, while FIG. 3 is a side view: of the proximal end of urethral catheter 28. As shown in FIG. 2, the distal end of urethral catheter 28 includes multi-port manifold 30, multi-lumen Shaft 32, connection manifold 34, cooling system 36, and microwave source 38.

Multi-port manifold 30 includes inflation port 40, urine drainage port 42A, microwave antenna port 44, coolant fluid receive port 46, and coolant fluid return port 48. Ports 40–48 communicate with corresponding lumens located within shaft 32.

Shaft 32 is connected to manifold 30 at shaft distal end 50. Shaft 32 is a multi-lumen, Foley-type urethral catheter shaft which is extruded from a flexible, medical-grade elastomer or thermoplastic. Shaft 32 has an outer diameter of about 20 French, and is both long enough and flexible enough to permit insertion of shaft proximal end 52 (shown in FIG. 3) through urethra 10 and into bladder 12. Shaft 32 can include a braid, plastic coating to provide stability and ensure proper insertion.

As shown in FIG. 3, urethral catheter 28 includes multi-lumen shaft 32, urine inlet 42B, retention balloon 51, shaft proximal end 52, first barrier 54, second barrier 56, ridges 58, sleeve 60, and outer thermal sensing lumen 61. First barrier 54, second barrier 56, ridges 58, and outer thermal sensing lumen 61 are formed from flexible, medical-grade elastomer or thermoplastic, similar to shaft 32. Sleeve 60 is formed from a polyethylene terepthalate (PET) material.

FIG. 4 is an enlarged, partial sectional view of a portion of urethral catheter 28 in which multi-lumen shaft 32, first barrier 54, second barrier 56, ridges 58, PET sleeve 60, outer thermal sensing lumen 61, apertures 62A and 62B, and chamber 63 are shown. During microwave thermal therapy, fluid is circulated from cooling system 36 (shown in FIG. 2) through the multi-port manifold 30 to multi-lumen shaft 32. The fluid is then forced through aperture 62& and fills chamber 63 enclosed by first barrier 54, second barrier 56, PET sleeve 60, and catheter shaft 32. As shown in FIG. 4, ridges 58 are located about shaft 32 at approximately 90° from one another. Ridges 58 do not fully extend from first barrier 54 to second barrier 56. Rather, ridges 58 alternate extending from either first barrier 54 or second barrier 56 and stop short of second barrier 56 or first barrier 54, respectively. This alternating pattern facilitates circulation of the fluid within PET sleeve 60 circumferentially about shaft 32. The fluid is then returned through second opening 62B (shown in phantom) to shaft 32. Outer thermal sensing lumen 61 contains a thermal sensor which monitors the temperature of urethra 10 during the therapy.

Figure 5A:
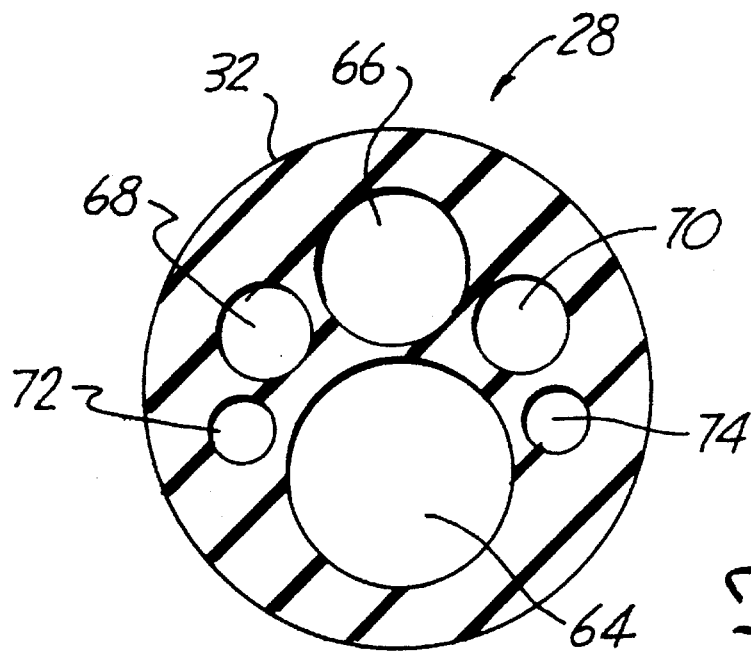
FIG. 5A is a cross-sectional view of the urethral catheter of FIG. 4 taken along line 5A—5A.

FIG. 5A is a cross-sectional view of urethral catheter 28 taken along line 5A—5A of FIG. 4. As shown in FIG. 5A, catheter shaft 32 includes microwave antenna lumen 64, urine drainage lumen 66, coolant fluid supply lumen 68, coolant fluid return lumen 70, inflation lumen 72, and inner thermal sensing lumen 74.

Microwave antenna lumen 64 is eccentrically located in relation to the longitudinal central axis of shaft 32. Microwave antenna lumen 64 is sealed at shaft proximal end 52 by a plug. Microwave antenna 76 (not shown in FIG. 5A) communicates with microwave source 38 (shown in FIG. 2). Microwave antenna 76 is permanently positioned within microwave antenna lumen 64 and is generally situated adjacent constriction 20 of prostate 14 when urethral catheter 28 is properly positioned within urethra 10. When microwave antenna 76 is energized by microwave source 38, microwave antenna 76 emits electromagnetic emissions to thermally damage tissue within prostate 14.

Urine drainage lumen 66 is located adjacent microwave antenna lumen 64. Urine drainage lumen 66 communicates with urine drainage port 42A (shown in FIG. 2) and urine inlet 42B (shown in FIG. 3) and defines a drainage path for urine when shaft proximal end 52 of shaft 32 is inserted within bladder 12. Drainage of urine from bladder 12 is necessary due to frequent bladder spasm which occurred during transurethral thermal therapy.

Figure 5B:
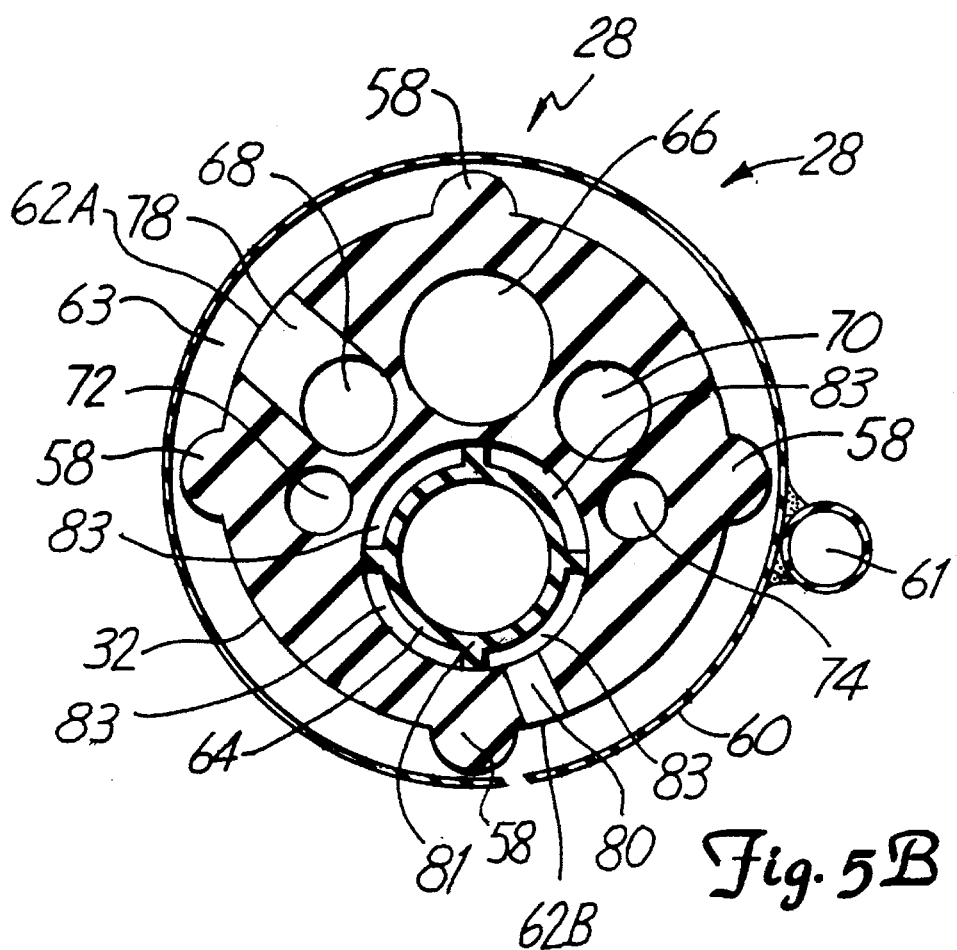
FIG. 5B is a cross-sectional view of the urethral catheter of FIG. 4 taken along line 5B—5B.

FIG. 5B is a cross-sectional view of urethral catheter 28 taken along line 5B—5B of FIG. 4. As shown in FIG. 5B, urethral catheter 28 includes, ridges 58, sleeve 60, outer thermal sensing lumen 61, apertures 62A and 62B, chamber 63, microwave antenna lumen 64, urine drainage lumen 66, coolant fluid return lumen 68, inflation lumen 72, inner thermal sensing lumen 74, fluid channels 78 and 80, antenna jacket 81, and coolant fluid supply shaft 83. Outer thermal sensing lumen 61 and inner thermal sensing lumen 74 contain a thermal sensor which monitors the temperature of urethra 10 during therapy. Antenna jacket 81 securely contains a microwave antenna (not shown in FIG. 5B) during therapy.

Fluid channel 80 provides a supply path for the cooling fluid between coolant fluid supply shaft 83 and chamber 63 while fluid channel 78 provides a return path for the cooling fluid between chamber 63 and lumen 68. The cooling fluid is circulated from coolant fluid supply shaft 83 into chamber 63 via aperture 62B and fluid channel 80. The cooling fluid fills chamber 63 defined by catheter shaft 32 and PET sleeve 60. The cooling fluid returns to catheter shaft 32 through coolant fluid return lumen 68 Via aperture 62A and fluid channel 78.

Figure 6:
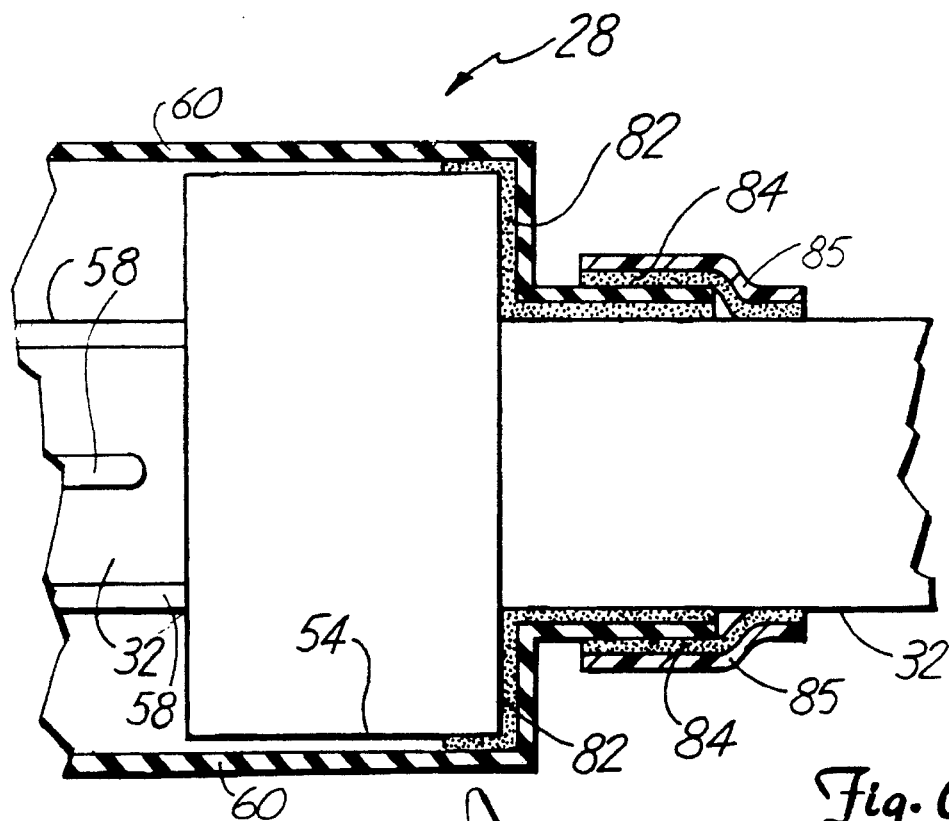
FIG. 6 is an enlarged pictorial view, shown partially in cross-section, of a portion of the urethral catheter of the present invention.

FIG. 6 is an enlarged pictorial view, shown partially in cross-section, of a portion of urethral catheter 28 showing PET sleeve 60 bonded to both first barrier 54 and multi-lumen shaft 32. The portion of urethral catheter 28 shown in FIG. 6 includes shaft 32, first barrier 54, ridges 58, PET sleeve 60, first adhesive bond 82, second adhesive bond 84, and sealing strip 85. PET sleeve 60 is bonded to first barrier 54 and catheter shaft 32 through use of first adhesive bond 82. Second adhesive bond 84 then lap bonds sealing strip 85 over PET sleeve 60 to ensure a quality bond. The bonding process utilizes medical-grade adhesive. A similar bonding process is completed where PET sleeve 60 is bonded to second barrier 56 and shaft 32.

Figure 7:
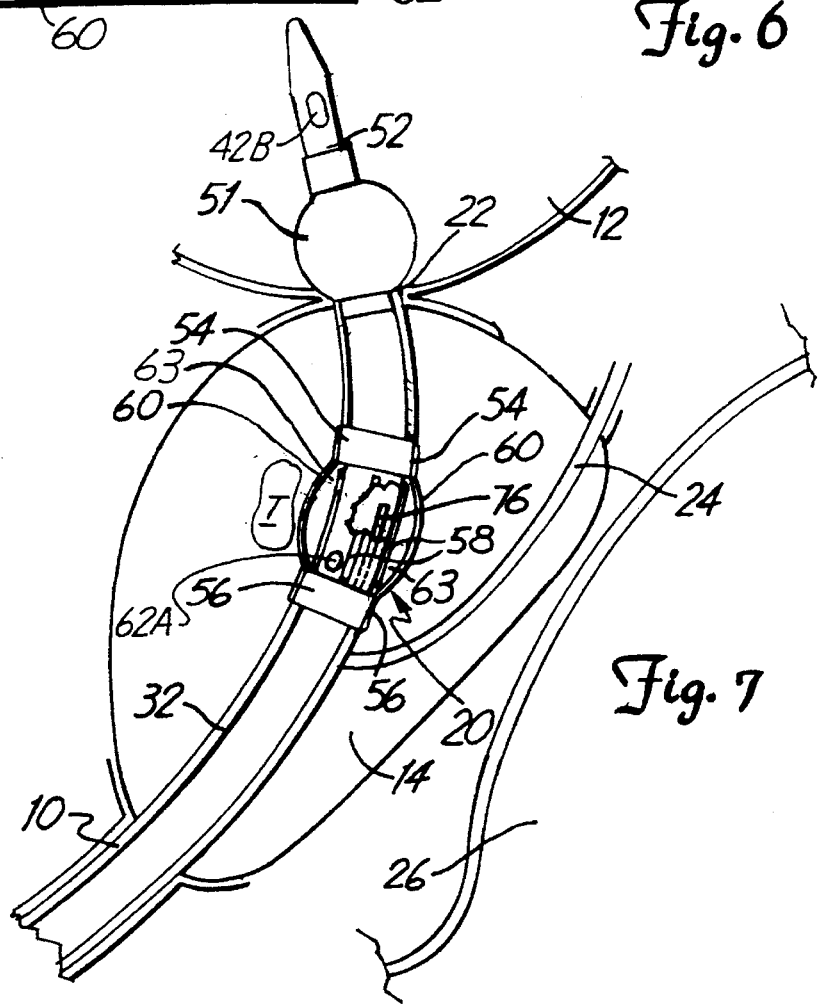
FIG. 7 is a diagram of the male pelvic region of FIG. 1 showing the urethral catheter of the present invention positioned within the prostate region.

FIG. 7 is a diagram of the male pelvic region showing urethral catheter 28 positioned within urethra 10 with first barrier 54 and second barrier 56 on opposite sides of tumorous tissue T, which causes constriction 20 (shown in FIG. 1). This ensures that microwave antenna 76 is positioned adjacent tumorous tissue T.

During transurethral thermal therapy, retention balloon 51 is inflated with fluid through use of inflation lumen 72 to hold urethral catheter 28 in position within urethra 10. Microwave antenna 76 emits microwave energy to thermally damage and necrose tumorous tissue T of prostate 14. The microwave energy heats benign tumorous tissue T to a temperature above approximately 45° C.

Cooling fluid is utilized to prevent thermal damage to healthy tissue (e.g., urethra 10) located between microwave antenna 76 and tumorous tissue T. Cooling fluid from cooling system 36 (shown in FIG. 2), is circulated into coolant fluid supply lumen 68 of multi-port manifold 30 via coolant fluid receive port 46. The cooling fluid is then circulated into multi-lumen shaft 32. The cooling fluid exits multi-lumen shaft 32 via fluid channel 78 and aperture 62A located between first barrier 54 and second barrier 56. The cooling fluid fills chamber 63 enclosed by first barrier 54, second barrier 56, PET sleeve 60, and shaft 32. The cooling fluid returns to coolant fluid return lumen 70 of catheter shaft 32 via opening 62B (not shown in FIG. 7) and fluid channel 80. The cooling fluid returns to cooling system 36 via coolant fluid return port 48 of multi-port manifold 30.

The cooling fluid circulating between first barrier 54, second barrier 56, PET sleeve 60, and shaft 32 cools and protects healthy, normal tissue located between urethral catheter 28 and tumorous tissue T of prostate 14. In particular, the urethral wall immediately adjacent PET sleeve 60 is cooled and thermal damage to the urethral wall is prevented.

FIGS. 8–13 show alternate embodiments of the present invention. In each of FIGS. 8–13, only the proximal portion of the urethral catheter is shown since the distal end is unchanged from what has previously been described. Similar reference numerals are used in all of the figures to designate similar elements.

FIG. 8 is a diagram illustrating a first alternate embodiment of the present invention. As shown in FIG. 8, urethral catheter 28 includes catheter shaft 32, retention balloon 51, shaft proximal end 52, first balloon 86, plurality of holes 88, and aperture 90. Urethral catheter 28 is shown positioned within urethra 10. During transurethral thermal therapy, retention balloon 51 is inflated with fluid through use of inflation lumen 72 and locates urethral catheter 28 within urethra 10. First balloon 86 is then inflated with fluid and forms a barrier between catheter shaft 32 and urethra 10. Retention balloon 51 and first balloon 86 are securely lap bonded to catheter shaft 32 by lap bond 91. Cooling fluid from cooling system 36 is circulated through coolant fluid supply lumen 68 of catheter shaft 32 to holes 88 and fills chamber 63 defined by catheter shaft 32, retention balloon 51, first balloon 86, and urethra 10. Therefore, the cooling fluid is in direct contact with urethra 10. The cooling fluid cools and protects healthy, normal tissue located between microwave antenna 76 and tumorous tissue T. In particular, the urethra wall is cooled and thermal damage to the urethra wall is prevented. The cooling fluid is recirculated through aperture 90 into coolant fluid return lumen 70 of catheter shaft 32 via fluid channel 80 and back to cooling system 36.

Since the cooling fluid is in direct contact with urethra 10, the temperature of the urethra wall is the same as the temperature of the cooling fluid. Therefore, a thermal sensor, outer thermal sensing lumen 61, and inner thermal sensing lumen 74 are not necessary in this embodiment. Rather, inner thermal sensing lumen 74 is transformed into an inflation lumen which facilitates inflation of first balloon 86 in this embodiment.

FIG. 9 is a diagram illustrating a second alternate embodiment of the present invention. The alternate embodiment shown in FIG. 9 is similar to the embodiment shown in FIG. 8; however, second balloon 92 has been added. During transurethral thermal therapy, retention balloon 51 is inflated through use of inflation lumen 72 and properly locates urethral catheter 28 within urethra 10. First balloon 86 and second balloon 92 are inflated through use of inflation lumen 74 and form barriers between catheter shaft 32 and urethra 10. Retention balloon 51, first balloon 86, and second balloon 92 are securely lap bonded to catheter shaft 32 by lap bond 91. Cooling fluid from cooling system 36 is then circulated into coolant fluid supply lumen 68 of catheter shaft 32. The cooling fluid is circulated through holes 88 via fluid channel 78, and fills chamber 63 defined by catheter shaft 32, first balloon 86, second balloon 92, and urethra 10. Therefore, the coolant fluid is in direct contact with urethra 16. The cooling fluid cools and protects healthy, normal tissue located between microwave antenna 76 and tumorous tissue T. In particular, the urethra wall is cooled and thermal damage to the urethra wall is prevented. The cooling fluid is recirculated through aperture 90 into coolant fluid return lumen 70 of catheter shaft 32 via fluid channel 80 and back to cooling system 36.

The embodiment shown in FIG. 10 is similar to the embodiment shown in FIG. 9; however, holes 88A and 88B have been replaced by first aperture 94 and second aperture 96. During transurethral thermal therapy, retention balloon 51 is inflated through use of inflation lumen 72 and is positioned within bladder 12. First balloon 86 and second balloon 92 are then inflated through use of inflation lumen 74. Retention balloon 51, first balloon 86, and second balloon 92 are securely lap bonded to catheter shaft 32 by lap bond 91. Cooling fluid is then circulated from coolant fluid supply lumen 68 of catheter shaft 32, through first aperture 94 to fill chamber 63 defined by first balloon 86, second balloon 92, catheter shaft 32, and urethra 10. The cooling fluid is then recirculated through second aperture 96 into coolant fluid return lumen 70 of catheter shaft 32, wherein the cooling fluid returns to cooling system 36.

The embodiment shown in FIG. 11 is similar to the embodiment shown in FIG. 10; however, the embodiment shown in FIG. 11 includes mesh braid 98. Mesh braid 98 ensures that the wall of urethra 10 will not collapse around catheter shaft 32 causing overheating and necrosing of urethra 10. Mesh braid 981has a constant tension in an outward direction. Therefore, once catheter 28 is in position, mesh braid 98 applies pressure to urethra 10 and forces it away from catheter shaft 32. This insures that cooling fluid can circulate within chamber 63 defined by first balloon 86, second balloon 92, catheter shaft 32, and urethra 10.

The embodiment shown in FIG. 12 is similar to the embodiment shown in FIG. 10; however, first balloon 86 is not permanently lap bonded to catheter shaft 32 at balloon end 100 and second balloon 92 is not permanently lap bonded to catheter shaft 32 at balloon end 102. Rather, first balloon 86 and second balloon 92 are valved at balloon ends 100 and 102, respectively. Once urethral catheter 28 is located within urethra 10, first balloon 86 and second balloon 92 are inflated with fluid through use of inflation lumen 74. At a point when first balloon 86 and second balloon 92 are filled with cooling fluid to capacity, balloon end 100 and balloon end 102 are forced open, shown in phantom, to allow cooling fluid to circulate within chamber 63 defined by first balloon 86, second balloon 92, catheter shaft 32, and urethra 10. First balloon 86 and second balloon 92 remain inflated during the therapy because the cooling fluid is supplied to first balloon 86 and second balloon 92 at a higher rate than the cooling fluid escapes through balloon ends 100 and 102. The cooling fluid recirculates through aperture 103, centrally located between first balloon 86 and second balloon 92, to coolant fluid return lumen 70 of catheter shaft 32.

The embodiment shown in FIG. 13 is similar to the embodiment shown in FIG. 12; however, first balloon 86 and second balloon 92 are securely lap bonded, not valved. During thermal therapy, once first balloon 86 and second balloon 92 are properly inflated, holes 104 within first balloon 86 and second balloon 92 are forced open to allow cooling fluid to circulate within chamber 63 formed by first balloon 86, second balloon 92, catheter shaft 32, and urethra 10. First balloon 86 and second balloon 92 remain inflated during the therapy because the cooling fluid is supplied to first balloon 86 and second balloon 92 at a higher rate than the cooling fluid escapes through holes 104. The cooling fluid recirculates through aperture 103 to coolant fluid return lumen 70 of catheter shaft 32.

The present invention is a urethral catheter which provides cooling fluid to a chamber located between the catheter shaft and the urethra wall. The catheter includes an antenna carried by the catheter shaft for delivering heat to intraprostatic tissue having benign prostatic hyperplasia surrounding the urethra. Cooling fluid is circulated through the catheter shaft to the chamber for cooling a portion of the urethra wall located adjacent the chamber, thereby preventing thermal damage to health, normal tissue located between the antenna and intraprostatic tissue.

Although the present invention has been described with reference to preferred embodiments, workers skilled in the art will recognize that changes may be made in form and detail without departing from the spirit and scope of the invention.

What is claimed is:

1. A method for treating tissue adjacent to a body lumen, the method comprising:

inserting a catheter having a catheter shaft into the body lumen;

delivering heat from the catheter to the tissue adjacent to the body lumen;

defining a chamber between the body lumen and the catheter shaft; and supplying a fluid to the chamber between the body lumen and the catheter shaft such that the fluid comes in direct contact with the body lumen to cool the body lumen.

2. The method of claim 1 wherein delivering heat to the tissue comprises generating an electromagnetic emission from an antenna located within the catheter shaft.

3. The method of claim 2 wherein the step of delivering heat includes heating the tissue to a temperature above approximately 45° C.

4. The method of claim 1 wherein defining a chamber comprises inflating a first balloon positioned between the catheter shaft and the body lumen and a second balloon positioned between the catheter shaft and the body lumen and located distally of the first balloon.

5. The method of claim 4 wherein supplying a fluid comprises:

circulating the fluid from the catheter shaft through at least one aperture in the catheter shaft located between the first and second balloons, wherein the fluid fills the chamber and comes in direct contact with the body lumen, and through a return aperture in the catheter shaft, wherein the fluid returns to the catheter shaft.

6. The method of claim 4 wherein supplying a fluid comprises:

circulating the fluid from the catheter shaft into the first balloon, through at least one aperture in the first balloon, wherein the fluid fills the chamber and comes in direct contact with the body lumen, and through a return aperture in the catheter shaft, wherein the fluid returns to the catheter shaft.

7. The method of claim 6 wherein supplying a fluid further comprises:

circulating the fluid from the catheter shaft into the second balloon, through at least one aperture in the second balloon, wherein the fluid fills the chamber and comes in direct contact with the body lumen, and through a return aperture in the catheter shaft, wherein the fluid returns to the catheter shaft.

8. The method of claim 4 wherein supplying a fluid comprises:

circulating the fluid from the catheter shaft into the first balloon, through a valved end of the first balloon, wherein the fluid fills the chamber and comes in direct contact with the body lumen, and through a return aperture in the catheter shaft, wherein the fluid returns to the catheter shaft.

9. The method of claim 8 wherein supplying a fluid further comprises:

circulating the fluid from the catheter shaft into the second balloon, through a valved end of the second balloon, wherein the fluid fills the chamber and comes in direct contact with the body lumen, and through a return aperture in the catheter shaft, wherein the fluid returns to the catheter shaft.

10. A device for treating tissue adjacent to a body lumen, the device comprising:

a catheter having a catheter shaft, the catheter shaft having an outer surface;

an antenna located within the catheter shaft for delivering heat to the tissue adjacent to the body lumen;

a first balloon located adjacent the outer surface of the catheter shaft for creating a first barrier between the catheter shaft and the body lumen;

a second balloon located adjacent the outer surface of the catheter shaft for creating a second barrier between the catheter shaft and the body lumen; and circulating means for circulating a fluid within a chamber defined by the first barrier, the second barrier, the outer surface of the catheter shaft and the body lumen such that the fluid comes in direct contact with the body lumen.

11. The device of claim 10 and further comprising:

a mesh braid connected to the outer surface of the catheter shaft between the first and second balloons for maintaining the chamber.

12. A method for treating tissue adjacent to a body lumen, the method comprising:

inserting a catheter having a catheter shaft into the body lumen;

delivering heat from the catheter to the tissue adjacent to the body lumen; and providing a cooling fluid through a chamber adjacent to the tissue adjacent the body lumen such that the fluid comes in direct contact with the body lumen, the chamber being defined by the catheter shaft and the body lumen.

13. The method of claim 12 wherein the step of providing a cooling fluid further comprises:

inflating a first balloon between the catheter shaft and the body lumen;

inflating a second balloon between the catheter shaft and the body lumen; and providing the cooling fluid between the first and second balloons adjacent to the tissue adjacent to the body lumen.

14. The method of claim 13 wherein the step of providing a cooling fluid further comprises:

circulating the fluid from the catheter shaft into the first balloon, through at least one aperture in the first balloon, wherein the fluid fills the chamber and comes in direct contact with the body lumen, and through a return aperture in the catheter shaft, wherein the fluid returns to the catheter shaft.

15. The method of claim 13 wherein the step of providing a cooling fluid further comprises:

circulating the fluid from the catheter shaft into the second balloon, through at least one aperture in a second balloon, wherein the fluid fills the chamber and comes in direct contact with the body lumen, and through a return aperture in the catheter shaft, wherein the fluid returns to the catheter shaft.

16. The method of claim 13 wherein the step of providing a cooling fluid further comprises:

circulating the fluid from the catheter shaft into the first balloon, through a valve in the first balloon, wherein the fluid fills the chamber and comes in direct contact with the body lumen, and through a return aperture in the catheter shaft, wherein the fluid returns to the catheter shaft.

17. The method of claim 13 wherein the step of providing a cooling fluid further comprises:

circulating the fluid from the catheter shaft into the second balloon, through a valved end of the second balloon, wherein the fluid fills the chamber and comes in direct contact with the body lumen, and through a return aperture in the catheter shaft, wherein the fluid returns to the catheter shaft.

18. A method for treating tissue adjacent to a body lumen, the method comprising:

inserting a catheter having a catheter shaft into the body lumen;

delivering heat from the catheter to the tissue adjacent to the body lumen;

inflating a first balloon positioned between the catheter shaft and the body lumen;

inflating a second balloon positioned between the catheter shaft and the body lumen, the second balloon located distally of the first balloon; and circulating a fluid from the catheter shaft through at least one aperture in the catheter shaft located between the first and second balloons, wherein the fluid fills the chamber and comes in direct contact with the body lumen, and through a return aperture in the catheter shaft, wherein the fluid returns to the catheter shaft.

* * * * *

UNITED STATES PATENT AND TRADEMARK OFFICE
CERTIFICATE OF CORRECTION

PATENT NO. : 5,575,811

DATED : NOVEMBER 19, 1996

INVENTOR(S) : JOHN M. REID, JAMES V. KAUPHUSMAN, CHRISTOPHER H. PORTER, BRUCE H. NEILSON

It is certified that error appears in the above-indentified patent and that said Letters Patent is hereby corrected as shown below:

Col. 2, line 6, after "C", delete "."

Col. 3, line 60, after "view", delete ":"

Col. 3, line 63, delete "Shaft", insert --shaft--

Col. 4, line 27, delete "62&, insert --62A--

Col. 6, line 59, delete "16", insert --10--

Col. 7, line 19, delete "981", insert --98--

Signed and Sealed this

Eleventh Day of March, 1997

Attest:

BRUCE LEHMAN

Attesting Officer

Commissioner of Patents and Trademarks